US007060147B2

(12) United States Patent
Reitmaier et al.

(10) Patent No.: US 7,060,147 B2
(45) Date of Patent: Jun. 13, 2006

(54) METHOD FOR THE APPLICATION OF A LAYER REMAINING PERMANENTLY ADHESIVE ONTO THE INSIDE OF A BREAST PROSTHESIS

(75) Inventors: Paul Reitmaier, Babensham (DE); Ulrike Esterer, Altenmarkt (DE); Nils Stelter, Flintsbach (DE); Georg Stuffer, Flintsbach (DE); Hans Stuffer, Nussdorf (DE)

(73) Assignee: Amoena Medizin-Orthopadie-Technik GmbH & Co., Raubling (DE)

( * ) Notice: Subject to any disclaimer, the term of this patent is extended or adjusted under 35 U.S.C. 154(b) by 14 days.

(21) Appl. No.: 10/267,349

(22) Filed: Oct. 9, 2002

(65) Prior Publication Data
US 2003/0038400 A1 Feb. 27, 2003

Related U.S. Application Data

(62) Division of application No. 09/930,006, filed on Aug. 15, 2001, now Pat. No. 6,494,912, which is a division of application No. 09/295,529, filed on Apr. 21, 1999, now Pat. No. 6,342,117.

(30) Foreign Application Priority Data
Apr. 21, 1998 (DE) ................ 198 17 769

(51) Int. Cl.
*B32B 37/00* (2006.01)
*A61F 2/52* (2006.01)
(52) U.S. Cl. .............. 156/145; 156/245; 156/290; 264/266
(58) Field of Classification Search .......... 156/145, 156/230, 241, 245, 290, 292; 264/266, 267, 264/263; 623/7
See application file for complete search history.

(56) References Cited

U.S. PATENT DOCUMENTS

| 4,247,351 | A | | 1/1981 | Rechenberg |
| 4,249,975 | A | * | 2/1981 | Rechenberg ................ 156/245 |
| 5,071,433 | A | | 12/1991 | Naestoft et al. .............. 623/7 |
| 5,171,321 | A | * | 12/1992 | Davis ............................ 623/7 |
| 5,352,307 | A | | 10/1994 | Wild ........................ 156/245 |
| 5,792,292 | A | | 8/1998 | Wild ........................ 156/145 |

(Continued)

FOREIGN PATENT DOCUMENTS

DE 2701627 7/1978

(Continued)

OTHER PUBLICATIONS

English language abstract for DE 4211542.

*Primary Examiner*—Geoffrey L. Knable
(74) *Attorney, Agent, or Firm*—Dilworth & Barrese LLP.

(57) ABSTRACT

A system is provided for application of a layer permanently adhering to the inside of a breast prosthesis formed as a shell-shaped body made from a soft-elastic material, in which a two-component silicone rubber forming the adhesive layer is injected into a mold prior to curing of the body and then cured together with the body. Alternatively, the two-component silicone rubber forming the adhesive layer is first cured in a shell, with the shell then being applied to the body in a mold and then cured again with the body. In a third alternative, the adhesive layer is cured while being joined to a carrier film, with the carrier film then being adhered to the prosthesis sheath which is then filled with addition-vulcanizing two-component silicone rubber and cured in a mold.

10 Claims, 3 Drawing Sheets

Figure 1:
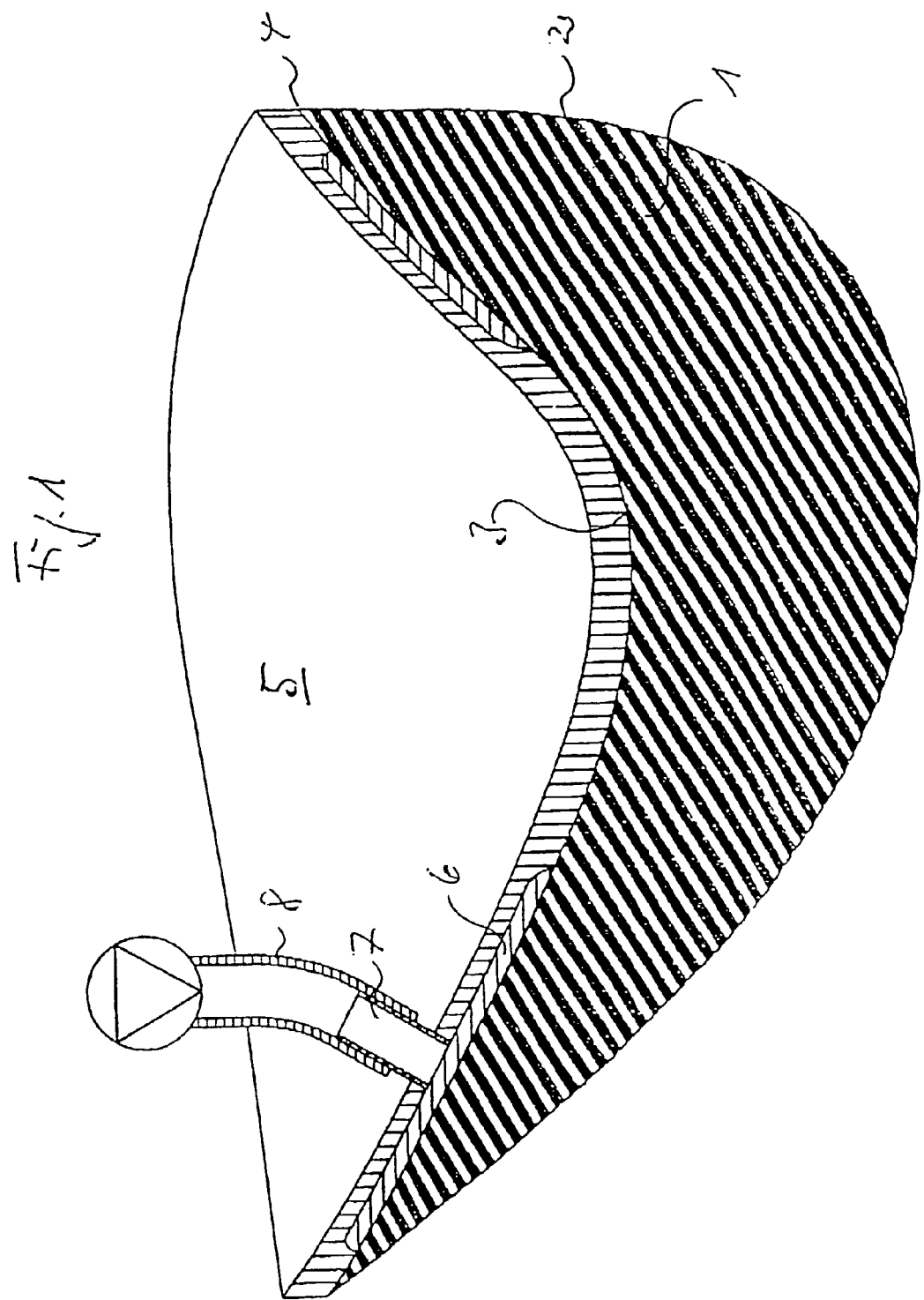

U.S. PATENT DOCUMENTS 5,922,023 A     7/1999   Mulligan et al.
5,925,282 A *   7/1999   Rasmussen .................. 249/55

FOREIGN PATENT DOCUMENTS

| DE | 2737321  | 3/1979  |
| DE | 3336279  | 5/1985  |
| DE | 3942608  | 7/1991  |
| DE | 4211542  | 5/1993  |
| DE | 93065728 | 12/1993 |
| DE | 29607969 | 6/1996  |
| DE | 29713203 | 9/1997  |
| EP | 542119   | 7/1997  |

* cited by examiner

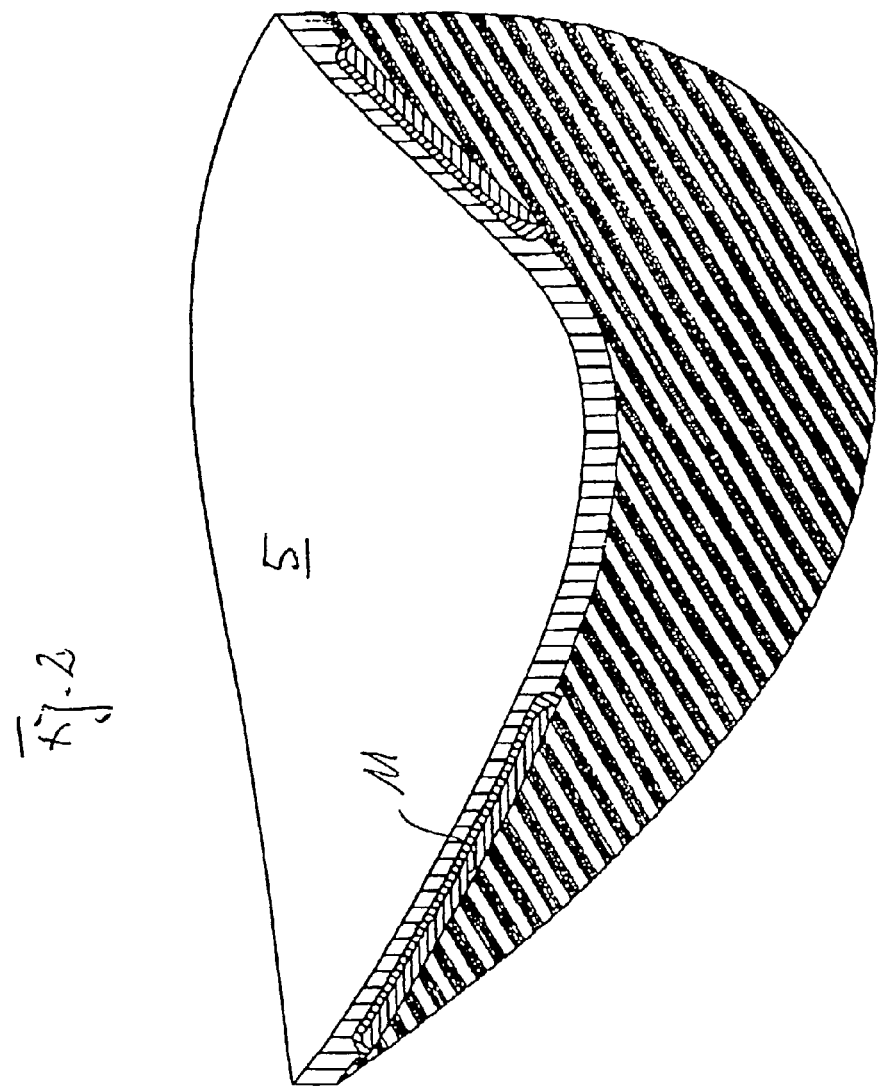
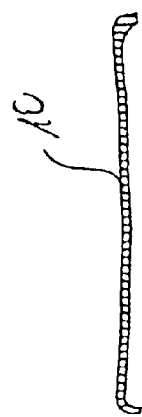
Fig. 2

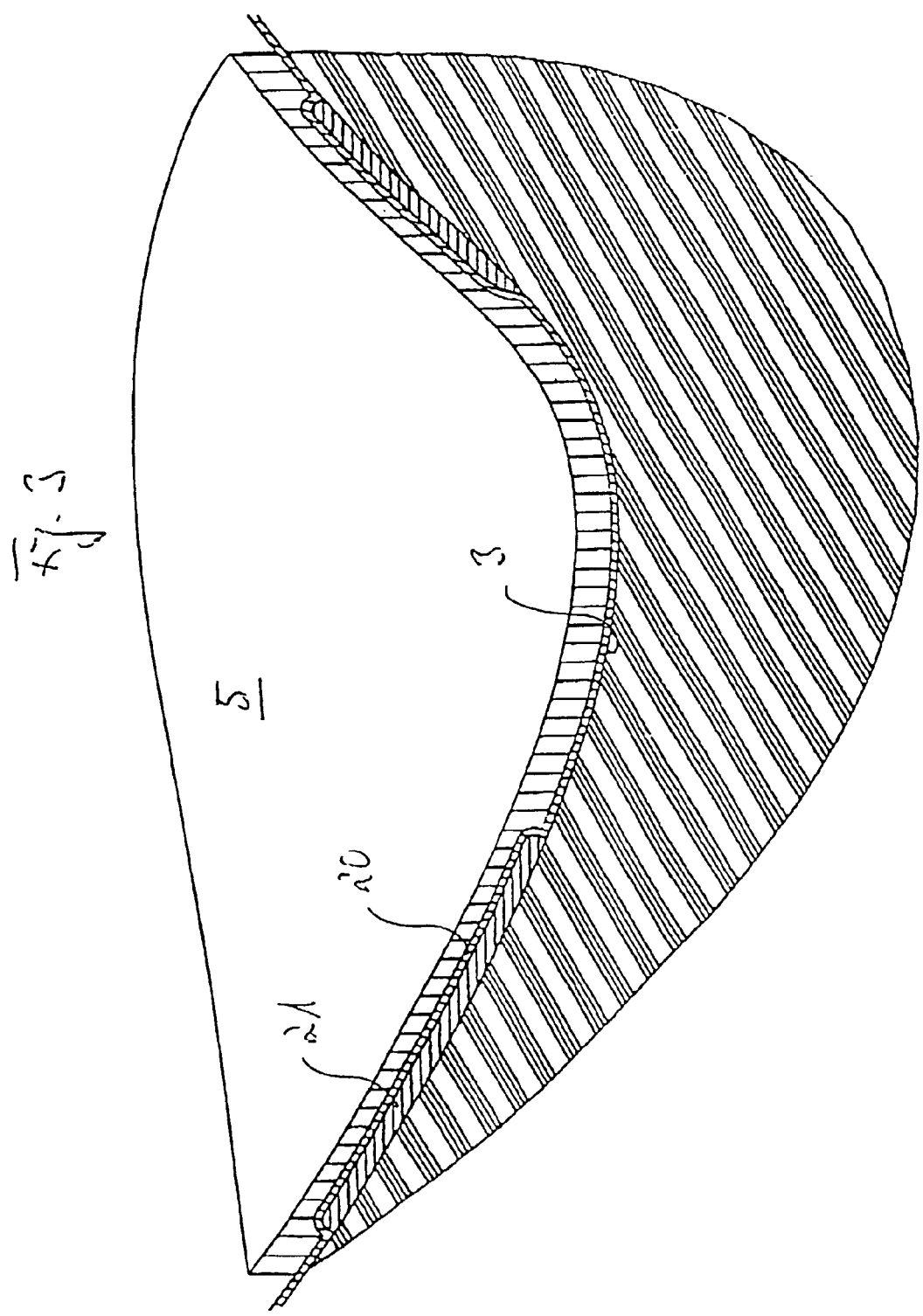

METHOD FOR THE APPLICATION OF A LAYER REMAINING PERMANENTLY ADHESIVE ONTO THE INSIDE OF A BREAST PROSTHESIS

Divisional of application Ser. No. 09/930,006 filed on Aug. 15, 2001 now U.S. Pat. No. 6,494,912 in turn a divisional application of application Ser. No. 09/295,529 filed on Apr. 21, 1999 and now U.S. Pat. No. 6,342,117 issued on Jan. 29, 2002.

The invention relates to a method for the application of a layer remaining permanently adhesive made from an adhesively set addition-vulcanising two-component silicone rubber mass onto the inside of a breast prosthesis consisting of a shell-shaped body made from a soft-elastic material, preferably of a body made from a soft-elastically set addition-vulcanising two-component silicone rubber mass which body is welded in plastic films which cover its outside and its inside and which is cured in a mould while heat is applied.

Methods of this type are known from EP 0 542 119 B1 according to which, on the one hand, an adhesively set addition-vulcanising two-component silicone rubber mass for the formation of the layer remaining permanently adhesive is introduced into a mould with a carrier film and is cured therein and subsequently the carrier film is glued or welded on its rear side in its edge region to the film enveloping the prosthesis and, on the other hand, an adhesively set addition-vulcanising two-component silicone rubber mass for the formation of the layer remaining permanently adhesive is introduced into a mould with a carrier film and is cured therein and a hot-melt adhesive is applied to the other side of the carrier film and subsequently the carrier film is applied to the film enveloping the rear side of the body and is joined to the film during the curing process of the body by the melting and solidifying of the hot-melt adhesive.

It is the object of the invention to propose further methods according to which layers remaining permanently adhesive can be joined to breast prostheses of the type first described in a simple and advantageous manner.

This object is solved in accordance with a first proposal by the two-component silicone rubber forming the adhesive layer being injected prior to the curing of the body through a borehole of the shell-shaped mould lid closing the mould, which mould lid is provided on its side facing the rear side of the prosthesis with a channel or recesses having a groove shape corresponding to the shape of the adhesive layer, and by its then being cured together with the body.

In accordance with this version of the method in accordance with the invention, the layer remaining permanently adhesive can be applied to the rear side of the prosthesis without the agency of a carrier layer. The adhesive layer can be applied circumferentially over the edge region of the rear side of the prosthesis or also only over a part of the edge region in the form of one or more spots. After the removal of the prosthesis from the mould, the adhesive layer can be covered by removable separating films so that it is protected until the prosthesis is put on. The mould lid covering the rear side of the prosthesis is provided in the region of the channel or recesses shaping the adhesive layer with a separating layer so that the adhesive layer does not stick to the mould lid when this is removed. If the mould lid is provided with multiple recesses forming the adhesive layer, these are connected to one another by channels or boreholes.

If the body of the breast prosthesis consists of a different soft-elastic material to a soft-elastically set addition-vulcanising two-component silicone rubber mass, said body can also be inserted into a mould and, after the application of the mould lid in the manner described, the layer remaining permanently adhesive can be applied which is subsequently cured in the mould.

In accordance with a second version, the object is solved in accordance with the invention by first the two-component silicone rubber forming the adhesive layer being cured in a shell made of elastic and/or plastic material having a recess or multiple recesses corresponding to the form of the adhesive layer and by the shell then being applied with the adhesive layer to the body lying in the mould bottom, the mould being closed by the mould lid and the adhesive strip being cured again with the body. Thanks to the second curing process, the adhesive layer joins to the film forming the rear wall of the prosthesis, which film normally comprises a PUR foil. After the removal of the mould lid, the shell, which appropriately comprises a thermoplastic plastic, can be pulled off so that it can be re-used. The layer remaining permanently adhesive is then protected in a usual manner by applying a separating layer.

In accordance with a third version, the object is solved in accordance with the invention by the adhesive layer being cured while joining with a carrier film and the carrier film being adhered to the later prosthesis sheath which is still lying flat and which is welded along a circumferential edge, and by the prosthesis sheath then being filled with the addition-vulcanising two-component silicone rubber and being cured in a mould.

The adhesive layer is manufactured separately in a known manner in a mould in which it joins with the carrier film.

The adhesive layer can already be applied with the carrier film to a film or film sheet before the prosthesis sheath is manufactured therefrom.

In accordance with a preferred embodiment, it is provided that the adhesive layer is applied directly to the sheath or the sheet before the manufacture of the sheath without the agency of a carrier layer.

In accordance with another preferred embodiment, it is provided that the adhesive layer is completely applied to the sheet forming the later rear side of the prosthesis prior to the manufacture of the sheath. If this film provided with the adhesive layer and forming the later rear side of the prosthesis is welded to the film forming the front side of the prosthesis along a circumferential edge, the weld tools press through the adhesive layer so that a good weld of the film sheets forming the flat-lying sheath is produced. After the manufacture of the prostheses, the layers remaining permanently adhesive are protected by separating films which are pulled off prior to the putting on of the prostheses.

In accordance with a fourth version, the object is solved by a removable film being applied to the film forming the rear side of the prosthesis in such a way that between the two films a channel corresponding to the form of the adhesive layer is formed, that the channel is filled with an addition-vulcanising two-component silicone rubber and this is then cured to the layer remaining permanently adhesive with the body in the mould. The removable film can remain on the rear side of the prosthesis and is removed by the wearer prior to the putting on.

In accordance with a fifth version, the object set is solved by an adhesive layer being manufactured in a separate mould with a central stiffening liner, protected on both sides by separating films and only being adhered on one side to the rear side of the prosthesis prior to the putting on of the prosthesis. The wearer pulls the separating film of one side off prior to the putting on of the prosthesis and adheres the inherently stable adhesive layer to the rear side of the prosthesis. Then she pulls off the second separating layer and can put on the prosthesis.

Appropriately, the liner comprises a textile liner. This has the advantage that the two-component silicone rubber can pass through the liner when the mould is filled to manufacture the adhesive layer and can spread out on both sides thereof.

The rear side of the prosthesis can be provided with an adhesive agent which effects a steady connection to the adhesive layer applied. In accordance with this aspect, it is ensured that the adhesive layer does not adhere to the body when the prosthesis is removed, but rather to the rear side of the prosthesis.

Embodiments of the invention are explained in more detail below by means of the drawing in which FIG. 1 shows a cross-section through a breast prosthesis lying in a mould (not shown) which is covered by a mould lid which is provided on its side facing the prosthesis with a channel corresponding to the adhesive layer to be applied;

FIG. 2 shows a representation of FIG. 1 in which between the mould lid and the rear side of the prosthesis a flexible strip with a recess in inserted which is filled with the adhesive strip; and FIG. 3 shows a representation of FIG. 1 in which a removable film is applied to the rear side of the prosthesis, between which film and the rear side of the prosthesis a channel corresponding to the shape of the adhesive layer is introduced which channel is filled with the two-component silicone rubber forming the adhesive layer.

In accordance with the embodiment of FIG. 1, into a bottom shell (not shown) of a mould a sheath filled with an addition-vulcanising two-component silicone rubber 1 is inserted which consists of a film 2 covering the front side of the prosthesis and a film 3 covering the rear side of the prosthesis which are welded to each other along their circumferential edge 4. The prosthesis sheath is manufactured from flat PUR films lying flat on top of one another prior to filling. The two-component silicone rubber is filled in through an edge opening so that due to the elasticity of the film material the prosthesis sheath assumes the shape of the later breast prosthesis.

The mould lid 5 possesses on its side facing the rear side of the prosthesis a flat recess 6 forming a channel, the shape of which recess is a negative shape of the adhesive layer to be applied to the rear side of the prosthesis. A connection 7 set into a borehole of the mould lid opens into the channel and to this connection a hose 8 is connected through which after the closing of the mould lid 5 the two-component silicone rubber forming the adhesive layer is filled via a pump into the groove-shaped recess 6.

After the closing of the mould and the introduction of the two-component silicone rubber forming the adhesive layer, this is cured in an oven in a usual manner together with the prosthesis body.

In the embodiment of FIG. 2, first in a special manufacturing process, a layer remaining permanently adhesive made from a two-component silicone rubber mass is manufactured in a flat shell of an elastic and/or plastic thermoplastic material having a groove-shaped recess which corresponds to the form of the later adhesive layer. The shell 10 with the adhesive layer 11 cured therein is then inserted into a cut-out of the mould lid 5 adapted to the shell shape and the mould is then closed with the thus prepared mould lid. The layer remaining permanently adhesive is then cured again in an oven together with the prosthesis body so that the adhesive layer joins with the film covering the rear side of the prosthesis. After the opening of the mould, the flat shell 10 is pulled off the adhesive layer so that it can be re-used. The adhesive layer manufactured in this way and joined with the rear side of the prosthesis is then covered by a separating film.

In the embodiment of FIG. 3, a removable separating film 20 is applied to the film 3 forming the rear side of the prosthesis, which separating film is joined to the film 3 in such a way that between the two a channel 21 is formed which corresponds to the form of the adhesive layer to be applied. Said channel 21 is filled prior to the closing of the mould with the mould lid 5 with a two-component silicone rubber mass forming the adhesive layer. A channel is worked into the mould lid which corresponds to the shape of the adhesive layer. After the channel is filled with the two-component silicone rubber mass forming the adhesive layer, said mass is hardened with the prosthesis body after the closing of the mould. The prosthesis can then be removed from the mould, with the adhesive layer being protected by the separating film 21 which is removed by the wearer only prior to the putting on.

The invention claimed is:

1. A method for producing a breast prosthesis with a single adhesive layer at its inside, said single adhesive layer remaining permanently adhesive, comprising the steps of
   forming a prosthesis sheath from plastic film material by welding the same at a circumferential edge,
   applying a single two-component silicone rubber mass layer directly to an exterior portion of said thus-formed prosthesis sheath,
   after applying the soft elastic material to the sheath portion, then filling a soft-elastic material into said prosthesis sheath, and
   after filling the soft elastic material into the sheath, then curing said soft-elastic material within said prosthesis sheath together with said single two-component silicone rubber mass layer in a shell-shaped mold.

2. A method in accordance with claim 1, wherein said soft-elastic material which is filled into said prosthesis sheath is made of a soft-elastically set addition-vulcanizing two-component silicone rubber mass.

3. A method according to claim 2, wherein said single two-component rubber mass layer is directly applied to the exterior portion of said thus-formed prosthesis sheath without agency of a carrier layer.

4. A method according to claim 1, wherein said single two-component rubber mass layer is directly applied to the exterior portion of said thus-formed prosthesis sheath without agency of a carrier layer.

5. A method for producing a breast prosthesis with a single adhesive layer at its inside, said single adhesive layer remaining permanently adhesive, comprising the steps of
   applying a single two-component silicone rubber mass layer directly to a plastic film material,
   after applying and curing the two-component silicone rubber mass to the plastic film material, then forming a prosthesis sheath from said plastic film material by welding the same at a circumferential edge,
   after forming the prosthesis sheath, then filling a soft-elastic material into said thus-formed prosthesis sheath, and
   after filling the soft elastic material into the sheath, then curing said soft-elastic material within said prosthesis sheath in a shell-shaped mold.

6. A method according to claim 5, wherein said step of applying a two-component silicone rubber mass to said plastic film material comprises application of said two-component silicone rubber mass to the whole surface of said plastic film material which is intended to form the inside portion of the breast prosthesis.

7. A method according to claim 6, wherein said single two-component rubber mass layer is directly applied to the plastic film material without agency of a carrier layer.

8. A method in accordance with claim 5, wherein said soft-elastic material which is filled into said prosthesis sheath is made of a soft-elastically set addition-vulcanizing two-component silicone rubber mass.

9. A method according to claim 8, wherein said single two-component rubber mass layer is directly applied to the plastic film material without agency of a carrier layer.

10. A method according to claim 5, wherein said single two-component rubber mass layer is directly applied to the plastic film material without agency of a carrier layer.

* * * * *